United States Patent [19]
Ulmer et al.

[11] Patent Number: 5,614,173
[45] Date of Patent: *Mar. 25, 1997

[54] HAIR SPRAY COMPOSITION HAVING 80% OR LESS VOC AND ADVANTAGEOUS PHYSICAL AND PERFORMANCE CHARACTERISTICS

[75] Inventors: Herbert Ulmer, Hoboken; Colleen M. Rocafort, Lake Hiawatha, both of N.J.

[73] Assignee: ISP Investments Inc., Wilmington, Del.

[*] Notice: The term of this patent shall not extend beyond the expiration date of Pat. No. 5,597,551.

[21] Appl. No.: 569,809

[22] Filed: Dec. 8, 1995

[51] Int. Cl.$^6$ .......................................... A61K 7/11
[52] U.S. Cl. ...................... 424/47; 424/78.02; 424/70.11; 424/DIG. 1; 424/DIG. 2; 514/957
[58] Field of Search ................................. 424/47, DIG. 1, 424/DIG. 2, 78.02, 70.11; 514/957

[56] References Cited

U.S. PATENT DOCUMENTS

| | | | |
|---|---|---|---|
| 4,897,262 | 1/1990 | Nandagiri et al. | 424/70.11 |
| 5,021,238 | 6/1991 | Martino et al. | 424/DIG. 2 |
| 5,094,838 | 3/1992 | Benson et al. | 424/DIG. 1 |
| 5,126,126 | 6/1992 | Varaprath et al. | 424/47 |
| 5,176,898 | 1/1993 | Goldberg et al. | 424/47 |

OTHER PUBLICATIONS

Martino, G.T. et al. (1992) *Spray Technology & Marketing*, Mar. Issue, pp. 34–39.
Johnsen, M.A. (1992), *Spray Technology & Marketing*, Jun. Issue, pp. 32–40.

*Primary Examiner*—Raj Bawa
*Attorney, Agent, or Firm*—Walter Katz; Marilyn J. Maue; Joshua J. Ward

[57] ABSTRACT

A hair spray composition of 80% or less VOC includes a fixative which is the half-ester of a copolymer of maleic anhydride and methyl vinyl ether having advantageous physical and performance properties even at low fixative levels. The copolymer is made by polymerizing the monomers at a selected temperature in the presence of a predetermined amount of a polymerization initiator whose decomposition fragments are soluble in hydroalcoholic solutions containing high levels of water. The composition is clear and without precipitate formation, has a low weight average molecular weight and a narrow molecular weight distribution or polydispersity, affording a low solution viscosity. The composition also forms a spray pattern of small particle size, providing clear, hard fixative films with superior adhesion to the hair of the user, an advantageous high humidity curl retention (hold), and low tack and dry times, in both pump and aerosol products.

17 Claims, No Drawings

HAIR SPRAY COMPOSITION HAVING 80% OR LESS VOC AND ADVANTAGEOUS PHYSICAL AND PERFORMANCE CHARACTERISTICS

BACKGROUND OF THE INVENTION

1. Field of the Invention

This invention relates to hair spray compositions, and, more particularly, to 80% or less VOC hair spray compositions which have advantageous physical and performance characteristics.

2. Description of the Prior Art

Copolymers of maleic anhydride and methyl vinyl ether, in the form of the $C_1$–$C_5$ alkyl half-ester, e.g. the ethyl half-ester, have been used extensively as the film-forming resin or fixative in hair spray compositions. Generally such ester copolymers have been prepared by polymerization of the monomers benzene or acetone solution in the presence of a free radical polymerization initiator followed by esterification. See Brit. Pats. 863,379; 1,233,468 and 712,220; Ger. Pat. 540,101; and U.S. Pat. Nos. 2,047,398; 4,908,413; 4,939,198; 5,139,034 and 5,223,567.

In general, free radical initiators used in such polymerization processes at elevated temperatures have included alkyl peresters, dialkyl peroxides, perketals, peroxydicarbonates, hydroperoxides, azo compounds and carbon-carbon labile compounds. Copolymerization also has been carried out at relatively low temperatures, e.g. room temperature, using a redox catalyst, such as, a combination of a redox catalyst and ascorbic acid, or, of a peroxydicarbonate and benzoin. It has been possible also to employ the polymerization initiator conjointly with a suitable accelerator, for example, an amine derived from a cyclic or phenyl structure, the amine being used by itself or together with an organic compound of a transition metal. Copolymerization also has been carried out with a mixture of different polymerization initiators having different decomposition temperatures.

The following compounds have been employed as initiators in free radical initiated polymerizations:
acetyl cyclohexanesulfonyl peroxide,
diacetyl peroxydicarbonate,
dicyclohexyl peroxydicarbonate,
di-2-ethylhexyl peroxydicarbonate,
tert-butyl per[oxy]-neodecanoate,
2,2'-azobis(4-methoxy-2,4-dimethylvaleronitrile);
tert-butylperoxy pivalate,
dioctanoyl peroxide,
dilauroyl peroxide,
2,2'-azobis-(2,4-dimethylvaleronitrile),
tert-butylazo-2-cyanobutane;
dibenzoyl peroxide,
tert-butylper[oxy]-2-ethylhexanoate,
tert-butylper[oxy]maleate,
2,2-azobis(isobutyronitrile);
bis(tert-butylperoxy) cyclohexane,
tert-butylperoxyisopropyl carbonate,
tertbutylper[oxy]acetate;
2,2-bis(tert-butylperoxy)butane,
dicumyl peroxide,
di-tert-amyl peroxide,
di-tert-butyl peroxide,
pinane hydroperoxide,
cumene hydroperoxide, and tert-butyl hydroperoxide.

Ethyl half-esters of copolymers of maleic anhydride and methyl vinyl ether (Gantrez® ES-225), may be prepared in acetone according to the free radical polymerization process described by Zamora et al., in U.S. Pat. No. 5,223,567, using decanoyl peroxide as the polymerization initiator. Such copolymers are supplied by International Specialty Products, Inc. as a 50% solids solution in ethanol.

Recent governmental legislation, however, has required that hair spray compositions contain only 80% or less volatile organic compounds (VOCs). Accordingly, it has been necessary for formulators of such hair spray products to substitute water for much of the ethanol solvent presently used to dissolve the hair fixative resin. However, an increase in the water content creates some significant problems, including:

A decrease in resin solubility

An increase in solution viscosity

An increase in spray particle size causing a poorer spray pattern

An increase in dry and tack times

A decrease in high humidity curl resistance (hold)

In aerosol formulations, the presence of water creates two additional problems:

Can corrosion

Solvent-propellant incompatibility.

Specifically, in a low VOC formulation, and particularly in a 55% VOC composition, which contains a very high water content, Gantrez® ES-225 forms only hazy compositions and has a high solution viscosity. These appearance properties are unacceptable commercially because of the cloudy appearance of the product and formation of a precipitate with time. In addition, such high viscosity formulations are difficult to spray adequately into spray patterns of fine particles. Accordingly, Gantrez® ES-225 has not been considered as a suitable fixative candidate for a 55% VOC hair spray product.

Goertz et al., in U.S. Pat. No. 4,908,413, described the preparation of ethyl half-ester copolymers of maleic anhydride and excess methyl vinyl ether by thermal polymerization of precharged monomers in acetone, followed by a second phase free radical polymerization. Esterification was carried out in ethanol in the presence of an esterification catalyst such as p-toluenesulfonic acid. However, the alcoholic solutions of such copolymers were considered as being only "equivalent in their physical properties and performance characteristics to the corresponding ones obtained by previous processes".

For these and other reasons, there has been an extensive ongoing research and development effort in both the chemical and cosmetic industries to find new polymers, and/or mixtures of polymers, which would provide acceptable 80% and 55% VOC hair spray compositions for the consumer.

Accordingly, it is an object of this invention to provide an 80% or less VOC hair spray composition, particularly a 55% VOC composition, which exhibits excellent performance properties, even at a low fixative solids level, and a clear fixative solution, without precipitate formation, and which has a low solution viscosity, a low copolymer weight average molecular weight and a narrow molecular weight distribution (MWD), and also which forms a spray pattern of small particle size, providing clear, hard fixative films with superior adhesion to the hair of the user, and which provides an effective high humidity curl retention (hold), as well as low tack and dry times, in both pump and aerosol hair spray products.

These and other objects and features of the invention will be made apparent from the following more detailed description of the invention.

SUMMARY OF THE INVENTION

What is described herein is a hair spray composition containing 80% or less VOC comprising, by weight, (a) about 0.5–12% of the ethyl or butyl half-ester copolymer of maleic anhydride and methyl vinyl ether, which is made by copolymerizing the monomers in a solvent at a predetermined temperature, in the presence of a selected amount of a polymerization initiator whose decomposition fragments in the solution are soluble in a 55% VOC hydroalcoholic composition, followed by esterification, preferably in the absence of an esterification catalyst, and wherein the copolymer solution is crystal clear, has a low weight average molecular weight of about 30,000 to about 120,000, preferably 50,000 to 100,000, and most preferably 60,000 to 80,000, a narrow polydispersity or molecular weight distribution (MWD) of less than about 2.5, preferably 1.8 to 2.2, and a solution specific viscosity of about 0.25 to 0.39, preferably 0.28 to 0.35, (i) optionally neutralized in an amount up to about 25 mole %, (b) 0–80% ethanol, (c) 19–99% water, and (d) 0–35% propellant.

The hair spray composition of the invention is crystal clear in appearance, has a Brookfield viscosity of less than 30 cps, preferably less than 20 cps, as a 5% solids solution, and forms clear, hard films having an effective high humidity curl retention (hold) of greater than 90%, a tack time of below 30 seconds, a dry time of below 45 seconds, and forms spray particles in pump systems having a size of less than 100 μm, and, in aerosol systems, of less than 80 μm.

DETAILED DESCRIPTION OF THE INVENTION

What has been discovered herein is that manufacture of alkyl half-esters of maleic anhydride and methyl or butyl vinyl ether according to Zamora, using decanoyl peroxide as the polymerization initiator, resulted in formation of initiator decomposition fragments which remained in the copolymer solution and were insoluble in water. Accordingly, it is these initiator decomposition fragments which caused hydroalcoholic solutions, and water-containing hair spray compositions, which have 80% or less VOC, particularly 55% or less VOC, containing such commercial copolymer solutions, to appear hazy and cloudy, and even to form a precipitate in time upon standing. In contrast, it has been found that the half-ester copolymer itself is readily soluble in 80% VOC or 55% VOC compositions. Such solutions appear crystal clear.

Accordingly, in this invention, water-compatible copolymers and solutions therefrom are made using polymerization initiators whose decomposition fragments are compatible in 80% or 55% VOC hydroalcoholic solutions and compositions. Suitable initiators include azobis compounds having a solubility of 0.5 g initiator/100 g water. These compounds can be present during polymerization in an amount of about 0.05% to about 10% by weight of the monomers used, preferably about 1 to about 5%.

Representative azo initiators for use herein thus include:

1,1'-azobis (1-cyclohexanecarbonitrile);

2,2'-azobis (N,N'-dimethyleneisobutyramidine) dihydrochloride;

2,2'-azobis(2-amidinopropane) dihydrochloride;

2,2'azobis(N,N'-dimethyleneisobutyramidine);

4,4'-azobis(4-cyanopentanoic acid);

2,2'-azobis{2-methyl-N-[1,1-bis(hydroxymethyl)-2-hydroxyethyl]propionamide};

2,2'-azobis{2-methyl-N-[1,1-bis(hydroxymethyl)ethyl] propionamide};

2,2'-azobis[2-methyl-N-(2-hydroxyethyl) propionamide; and 2,2'-azobis(isobutyramide) dihydrate.

Other azo initiators which have a solubility in water lower than 0.5 g/100 g water but their decomposition products are suitably soluble in hydroalcoholic solutions also may be used. Such azo initiators include:

2,2'-azobisisobutyronitrile;

2,2'-azobis-(2,4-dimethylvaleronitrile);

2,2'-azobis(4-methoxy-2,4-dimethylvaleronitrile);

1,1'-azobis-(1-cyclohexanecarbonitrile); and dimethyl-2,2'-azobis-(isobutyrate).

Copolymers made using suitable azo initiators, and their solutions and hair spray compositions, have advantageous physical and performance properties as compared to copolymer solutions and hair spray compositions prepared by either the Zamora or Goertz processes.

In particular, the copolymers of this invention have a low weight average molecular weight and narrow polydispersity or molecular weight distribution, which provides hair spray compositions having a desirable low viscosity suitable for forming advantageous spray particles of small size, in both pump and aerosol systems. With these copolymer solutions and compositions, the consumer can experience an exceptional holding power on the hair, while affording acceptable tack and dry times.

In this invention, the weight average molecular weight and polydispersity of the copolymer may be controlled by using a predetermined amount of the azo initiator during polymerization, and by selection of a suitable polymerization temperature. For example, for a selected low weight average molecular weight of about 50,000 to 80,000, and a polydispersity of about 1.8 to 2.2, a suitable amount of an azo initiator having a 10-hour half-life of about 60° to 70° C. is about 1 to about 5% by weight of the maleic anhydride monomer present during polymerization, and the polymerization temperature is about 60° to about 90° C.

Furthermore, the advantageous physical and performance properties of the half-ester copolymer of the invention in hair spray compositions also is enhanced herein by carrying out the polymerization step by free radical polymerization only, which reduces the weight average molecular weight of the copolymer. Preferably, esterification is carried out in the absence of an esterification catalyst. Such acid catalysts remain in the resultant ester copolymer solution and produce a hazy film when cast from hydroalcoholic solutions of high water content. Furthermore, the presence of an esterification catalyst will produce significant amounts of the diester copolymer, which is undesirable because it is less water compatible than the half-ester copolymer. The diester also has a reduced Tg so that its fixative film is softer than the half-ester copolymer of this invention.

If desired, the half-ester copolymer solution herein may be neutralized up to about 25 mole % with a suitable neutralizing agent, such as triisopropanol amine (TIPA), 3-aminopropanol (AMP-95), $NH_4OH$ or NaOH, and the like. In general, a higher degree of neutralization will be used in a hair spray composition containing a higher water content.

The invention will now be described in detail by reference to the following examples.

EXAMPLE 1 (INVENTION)

Preparation of the Ethyl Ester of a Maleic Anhydride-Methyl Vinyl Ether Copolymer in Ethanol

(a) Copolymerization

A pressurized reactor vessel was precharged with 7819 lbs of acetone and maintained at 70°–80° C. with agitation under a nitrogen atmosphere. Then separate streams of 5225 lbs of molten maleic anhydride (MA), 3713 lbs of liquid methyl vinyl ether (MVE) and a solution of 209 lbs. of 4,4'-azobis(4-cyanopentanoic acid) in 1033 lbs of acetone, (4% by weight based on MA) were introduced separately and continuously into the precharged reactor.

The MA addition rate was 15.47 lb/min; the MVE addition rate was 21.77 lb/min; and the initiator solution addition rate was 5.18 lb/min. The period of addition was 6 hours. The product was clear and odorless, viscous, 50% solids acetone solution of the maleic anhydride-methyl vinyl ether copolymer having a specific viscosity of about 0.3 and less. Residual monomers, acetone and maleic acid were substantially absent from the solution.

(b) Esterification and (c) Solvent Exchange

The copolymer solution (in acetone) then was esterified and solvent exchanged with ethanol by injecting vaporized ethanol at 85°–95° C. continuously through spargers below the surface of the solution over an 8 hour period while simultaneously distilling acetone overhead at atmospheric pressure at the boiling point of the solution (approximately 60° C.). The product was a crystal clear, odorless ethanol solution of the ethyl half-ester of the copolymer, at a 50% solids level, with less than 0.2% acetone therein, and substantially no residual monomers or maleic acid, at a specific viscosity of about 0.4 or less.

COMPARATIVE EXAMPLES

EXAMPLE 2 (ZAMORA)

Zamora, U.S. Pat. No. 5,233,367, Example 1 (which used decanoyl peroxide as the polymerization initiator) was repeated to provide the ethyl half-ester copolymer of maleic anhydride and methyl vinyl ether as a 50% solution in ethanol. A hair spray composition was prepared at 55% VOC using this copolymer solution, and its properties were determined in comparative testing with similar hair spray compositions containing the copolymer solution of the invention.

EXAMPLE 3 (GOERTZ)

Goertz, U.S. Pat. No. 4,908,413, Example 1 (which used 2,2'-azobis-(2,4-dimethylvaleronitrile as polymerization initiator and p-toluenesulfonic acid as the esterification catalyst) was repeated to provide an ester copolymer of maleic anhydride and methyl vinyl ether as a 50% solution in ethanol. Then a hair spray composition was prepared at 55% VOC using this copolymer solution, and its properties were determined in comparative testing with the composition of this invention.

INVENTION COMPOSITIONS

Several pump and aerosol compositions containing the invention were prepared, and are shown in Table 1 below.

TABLE 1

| 55% VOC Hair Spray Compositions of Invention | | |
|---|---|---|
| Pump* | | |
| | % by Wt. | |
| Components | (A) | (B) |
| Copolymer of Ex. 1 (as 100% solids) | 4.0 | 4.0 |
| AMP-95 | — | 0.18 |
| TIPA | 0.38 | — |
| Ethanol (total) | 55.0 | 55.0 |
| Water | 40.62 | 40.82 |
| pH | 5.40 | 5.55 |

*Seaquist Euromist II (160 mcl output) with 0.018" × 0.010" deep actuator.

| Aerosol** | | |
|---|---|---|
| | (A') | (B') |
| Copolymer of Ex. 1 (as 100% solids) | 5.0 | 5.0 |
| AMP-95 | 0.23 | 0.23 |
| Ethanol (total) | 20.0 | 20.0 |
| Water | 39.17 | 8.92 |
| Corrosion Inhibitors | | |
| Liquid phase (MEA-Borate and MIPA-Borate Menacore ® BE) | 0.40 | 0.40 |
| Vapor phase (NH₄OH) | 0.20 | 0.20 |
| Propellant | | |
| DME (Dimethyl ether) | 35.00 | — |
| HFC-152A (duPont) | — | 30.00 |

| (A) | (B) |
|---|---|
| **Seaquist ST-74 Valve 0.018 × CAP × 0.015 VT × 0.050 ID Actuator: ST-150 Misty Orifice: 0.023" | **Seaquist ST-74 Valve 0.013 × 0.062 Std × No VT × 0.122 ID Actuator: ST-200 Misty Orifice: 0.018" |
| pH (of concentrate, without propellant) 6.5 | 6.6 |

In high solids hair spray formulations, e.g. at 10–12% solids, a suitable spray is made by using suitable atomizer equipment, as follows:

For aerosols: a Seaquist ST-74 valve system having a 0.010" stem/cap body/0.010" VT/0.030"ID; Actuator: ST-150 Misty, 0.020" orifice.

Spray rate: 0.25"–0.28"

Pattern: 3½–4"

PROPERTIES OF COPOLYMERS OF INVENTION

Table 2 summarizes the weight average molecular weights, polydispersity and specific viscosities for the various examples. As can be seen from Table 2, the invention possesses the lowest weight average molecular weight and specific viscosity values, namely, 63,900 and 0.28, respectively, as compared to the other examples. The invention example also possesses the narrowest polydispersity of 2.0.

TABLE 2

PHYSICAL PROPERTIES OF COPOLYMERS OF
INVENTION AND COMPARATIVE COPOLYMERS

| Copolymer | Weight Average Molecular Wt,* $M_w$ | Polydispersity, $M_w/M_n$ | Specific Viscosity** |
|---|---|---|---|
| Invention (Example 1 herein) | 63,900 | 2.0 | 0.28 |
| Zamora (Example 2 herein) | 82,700 | 3.2 | 0.35 |
| Goertz (Example 3 herein) | 160,000 | 3.2 | 0.99 |

*based on polystyrene calibration curve
**1 wt. % solution of copolymer in ethanol Table 3 presents the user performance characteristics of 55% VOC pump hair spray compositions containing (A) Gantrez® ES-225 copolymer, in ethanol, with copolymers prepared according to (B) Zamora or (C) Goertz, compared to (D) the Invention. As shown therein, the low weight average molecular weight and narrow polydispersity of the invention copolymers provides performance attributes in the respective formulations which are superior to those containing Gantrez® ES-225, or the Zamora or Goertz copolymer solutions. The low specific viscosity of formulations utilizing the invention copolymer solution also reduces tack and dry times of the system, and provides a very desirable spray pattern.

TABLE 3

COMPARISON OF USER PERFORMANCE OF
55% VOC PUMP HAIR SPRAY COMPOSITIONS

|  | (A) Gantrez® ES-225 (100% VOC) | (B) Zamora (55% VOC) | (C) Goertz (55% VOC) | (D) Invention* (55% VOC) |
|---|---|---|---|---|
| % Active (polymer solids) | 5.5% | 4.0% | 4.0% | 4.0% |
| Film Hardness (70F/50% RH) 9H = Very Hard 1B = Very Soft | 3H–4H | 6H | 9H | 5H |
| Film Clarity (70F/50% RH) | Clear | Sl. Hazy | Sl. Hazy | Clear |
| HHCR (Hold) (80F/90% RH) @ 90 minutes | 95.35% | 98.03% | 96.06 | 98.52% |
| HHCR (80F/90% RH) @ 4 hrs | 92.61% | 96.03% | 94.60% | 96.15% |
| Duration of Tack | 18 secs | 42 secs | 36 secs | 23 secs |
| Dry Time | 39 secs | 54 secs | 65 secs | 44 secs |

COMPARISON OF USER PERFORMANCE OF VARIOUS
55% VOC PUMP HAIR SPRAY COMPOSITIONS

|  | (A) Gantrez® ES-225 (100% VOC) | (B) Zamora (55% VOC) | (C) Goertz (55% VOC) | (D) Invention (55% VOC) |
|---|---|---|---|---|
| Stiffness 10 = Very very Stiff 1 = Very very Soft | 6 | 7.6 | 8.0 | 8 |
| Non-Flaking 10 = No Flaking 1 = Heavily Coated | 9 | 9.2 | 7.2 | 8.6 |
| Ease of Combing 10 = No Drag 1 = Very heavy drag | 6.8 | 6.6 | 8.6 | 6.2 |
| Removability | Acceptable | Acceptable | Acceptable | Acceptable |
| Particle Size D[v, 0.5] | 80 microns | 105 microns | 143 microns | 83 microns |
| Spray Pattern @ 6" | 2.5–3" | 3½–4 | 3½" | 3.5" |
| Spray Character | Fine spray | Coarse spray | Coarse spray | Very fine spray |
| Initial Curl Droop (70F/50% RH) @ 10 minutes | 6% | 28% | 10% | 7% |

*Copolymer is 10% neutralized
PUMP: Seaquist Euromist II (160 mcl output) with 0.018" × 0.010" deep actuator More particularly, as shown in Table 3 above, the invention compositions (D) provide crystal clear hair spray compositions, with a hold of >90%, a tack time of <30 seconds, a dry time of <45 seconds, and a pump particle size of <100 μm, as fine particles. In contrast, Zamora's hair spray compositions (B) are hazy, provide less than 90% hold, a tack time of greater than 40 seconds, a dry time of greater than 60 seconds, and only coarse spray particles of greater than 100 μm in size. Hair spray compositions prepared using the Goertz copolymer solution (C) also have a slight haze, an extended tack time of 36 seconds, a very long dry time of 65 seconds, and a particle size of 143 μm, and coarse in appearance. Accordingly, the copolymer solutions of the invention, and 55% VOC hair spray compositions made therefrom, exhibit physical and performance characteristics which are commercially acceptable, whereas both Gantrez® ES-225, and the Zamora and Goertz copolymer solutions and compositions, provide much poorer and less acceptable products.

From Table 3, also, it is seen that the invention provides a desirable low initial curl droop in 55% VOC formulations of 7%, which is comparable to anhydrous systems, while formulations utilizing the Zamora and Goertz copolymers give an initial curl droop of 28% and 10%, respectively.

As discussed, the initiator residues of decanoyl peroxide are responsible for the unacceptable haze/precipitate in formulations utilizing the Zamora copolymer which contain a high percentage of water. These initiator residues, e.g. ethyl decanoate, also appear to plasticize the copolymer and may contribute to the observed extended tack and dry times, soft films and the high initial curl droop for hair spray compositions containing such copolymer solutions.

A similar study for aerosol compositions is given in Table 4 below. The results parallel those for pump systems.

TABLE 4

COMPARATIVE AEROSOL HAIR SPRAY COMPOSITIONS

|  | (A)<br>Gantrez ® ES-225<br>(100% VOC,<br>4% Active) | (B)<br>Invention<br>Copolymer<br>35% DME<br>(55% VOC,<br>5% Active) | (B')<br>Invention<br>Copolymer<br>30% 152a<br>(55% VOC,<br>5% Active) |
|---|---|---|---|
| Film Hardness<br>(70F/50% RH)<br>9H = Very Hard<br>1B = Very Soft | 9H | 9H | 9H |
| Film Clarity<br>(70F/50% RH) | Clear | Clear | Clear |
| HHCR, %<br>(80F/90% RH)<br>@ 90 minutes | 100 | 98.81 | 100 |
| HHCR, %<br>(80F/90% RH)<br>@ 4 hrs | 84.39 | 89.32 | 98.75 |
| Duration of Tack, sec. | 8.4 | 7.2 |  |
| Dry Time | 49.8 | 13.0 | 20.8 |
| Stiffness<br>10 = Very very Stiff<br>1 = Very very Soft | 65.6<br>8.4 | 22.0<br>7.2 | 33.2<br>8.2 |
| Non-Flaking<br>10 = No Flaking<br>1 = Heavily Coated | 8.8 | 8.8 | 8.4 |
| Ease of Combing<br>10 = No Drag<br>1 = Very heavy drag | 6.8 | 8.0 | 6.4 |
| Removability | Acceptable | Acceptable | Acceptable |
| Particle size<br>D[v, 0.5] | 97 microns | 38 microns | 69 microns |
| Spray Pattern, @ 6" | 4" | 4" | 4.5" |
| Spray Character | Very fine spray | Fine spray | Fine spray |
| Spray Rate<br>(grams/sec) | 0.54 | 0.60 | 0.90 |
| Valve/Actuator |  | Seaquist ST-74<br>0.018 × Capillary ×<br>0.015 VT × 0.050<br>ID ST-150 Misty<br>0.023" | Seaquist ST-71<br>0.013 × 0.062 Std ×<br>NO VT × 0.122<br>ID ST-200 Misty<br>0.018" |

The invention copolymer solutions may be used at VOC levels up to 80% VOC, as described in Table 5 below.

TABLE 5

70% VOC AND 80% VOC INVENTION COMPOSITIONS

|  | at 70% VOC | at 80% VOC |
|---|---|---|
| Film Clarity | 2 | 3 |
| Hard Film | 9H | 9H |
| Acceptable pH | 4.3 | 4.55 |
| Long Term HHCR-90 min | 100.00 | 100.00 |
| Long Term HHCR-4 hr | 98.21 | 99.43 |
| Drying (Dry Time) | 46.4 | 46.0 |
| Tack (Duration) | 32.8 | 33.0 |
| Stiffness | 6.8 | 6.0 |
| Comb | 7.6 | 8.0 |
| Hair | 9.2 | 8.8 |
| Shine | 9.2 | 9.6 |

TABLE 5-continued

70% VOC AND 80% VOC INVENTION COMPOSITIONS

|  | at 70% VOC | at 80% VOC |
| --- | --- | --- |
| Combability | 7.6 | 7.4 |
| Curl Snap | 8.4 | 7.0 |
| Manageability | 6.2 | 3.4 |
| Static | 3.2 | 3.6 |
| Particle Size D[v,0.5] | 83.30 microns | 86.13 microns |
| Spray Pattern | 4-½" | 4-½" |
| Sprayability | fine spray w/spots | fine spray w/spots |
| Rate (g/sec) | 0.13 | 0.13 |

In summary, the low solution viscosities of hair spray compositions containing the copolymer solution of the invention improves the spray characteristics of the hair spray formulation resulting in excellent particle size and leading to improved tack and dry times. Such formulations, even at low solution viscosities, also show excellent hair hold under normal usage levels. The narrow polydispersity of the invention copolymers also maximizes the use of an optimized average molecular weight for an enhanced hold property while minimizing the amount of low molecular weight fractions, which might plasticize the film and reduce hold. The substantial absence of high molecular weight fractions in the copolymer of the invention also is advantageous because such fractions produces undesirable viscosity fluxes and negatively affect spray aesthetics. In addition, the low viscosity of high solids formulations of the copolymer solutions herein provides a stiffer hold characteristic for the user.

APPENDIX

The following test protocols were used herein; other property and performance characteristics were obtained by standardized test procedures.

1. SOLUBILITY

To determine whether copolymers and polymer solutions were soluble in 80% VOC or lower ethanol/water solutions, the following procedure was used.

PROCEDURE:

1. Prepare an 80% VOC or lower VOC hair spray formulation with the "test" copolymer.
2. Neutralize the copolymer as necessary with a base.
3. Visually examine the finished prototype and rate the test solution as follows:

RATING:

Clear—Polymer completely soluble.

Hazy—Polymer dissolved; but solution is hazy in appearance.

Insol/PPT—Polymer is not soluble; and precipitates out of solution.

2. HIGH HUMIDITY CURL RETENTION

The curl retention properties of styling or finishing products containing resins are measured at 80±2 F/90±2% RH over a specified period. The change in percentage curl retention versus time is plotted to illustrate differences among various formulations.

EQUIPMENT

Duco Cement
8" European Brown Hair
Scissors
Nylon Comb
Plexiglass cut to 1" squares
2⅞"×⅝" blue curler and metal clips or ⅝"
Plexiglass mandral, and retention boards with ¼" markings
Environmental Chamber (with precision of ±2% RH and 80±2 F) Shampoo

| PROCEDURE: | |
| --- | --- |
| A. | Preparation of Hair Swatches |
| 1. | Separate hair into swatches, 2 grams in weight. |
| 2. | Glue the root ends onto a 1" plexiglass square. Allow glue to dry completely. |
| 3. | Comb tresses to remove excess hair. |
| 4. | Cut each hair swatch to measure 6.5" in length from the bottom of the plexiglass square to the end of the tress. Be sure that the length of all of the tresses used is the same length. Your initial length is referred to as Lo. |
| 5. | Wash hair swatches in 10% shampoo solution (reviving, lite or EFA shampoos are acceptable; but make sure the same shampoo is used for all testing). |
| 6. | Rinse tresses thoroughly with warm tap water. |
| 7. | Comb through to untangle hair tresses. |

| B. | Preparation and Exposure of Test Samples |
| --- | --- |
| 8. | Squeeze out excess water by running tress between your thumb and index finger. NOTE: Tresses must be prepared one day prior to testing and cannot be used if in rollers longer than 24 hours |
| 9. | Check chamber for conditions (80 + 2 F/90 + 2% RH). Adjust as necessary and allow chamber to equibrate prior to preparing tresses for testing. |
| * | Check (Section C) below for application of products prior to curling hair |
| 10. | Curl hair in a coil configuration by rolling it on a diagonal onto a ⅝" curler. Secure hair on curler with a metal clip. |
| 11. | Dry hair in the curler at room temperature overnight on a horizontal surface, or suspend from hooks under bonnet dryer for one (1) hour, except for gel and mousse. Curls treated with gel or mousse must be dried in oven set at 100° C. for one (1) hour and then dried at room temperature overnight on a horizontal surface. |
| 12. | The next day, carefully remove clip and slide the curler out of the hair. |
| 13. | Suspend the curled tress from the plexiglass end and apply a controlled amount of product as discussed below. |
| 14. | Lay the treated curls on a horizontal surface and allow to air dry for ½ hour except as stated below for gels and mousse. |
| 15. | Suspend the dry treated curls in a random fashion from graduated, plexiglass retention boards. |
| 16. | Recheck chamber for conditions prior to placing boards in chamber. |
| 17. | Take initial readings of the curl heights prior to placing boards in the chamber. These readings are referred to as Li. |
| 18. | Place boards in chamber and close door. Do not open chamber until testing is completed. |
| 19. | Record curl heights at specific time intervals. These readings are referred to as Lt. |

Time intervals are 15, 30 minutes, 1, 1½, 2, 3, 4, 6 hours or longer if required.

NOTE: For Spritz, gel and mousse record data only up to 4 hours. For screening purposes, 90 minutes may be used; for decision making purposes four (4) hours is preferred.

C. Application of Products

| Product | Amount to Apply |
|---|---|
| Aerosol Hair Spray | Two (2) second burst evenly applied to both front and back of curled tress at a distance of 8". |
| Pump Hair Sprays | Two (2) sprays delivered uniformly to both front and back of curled tress at a distance of 8". |
| Spritz Type Products | Two (2) sprays delivered uniformly to both front and back of curled tress at a distance of 8". |
| Gels | 0.50 grams of product is applied to wet hair, and combined through to evenly distribute. Hair is then rolled onto curler as specified and dried in a 100° C. oven for one (1) hour, then overnight at room temperature on a flat surface. |
| Mousse | 0.50 grams of product is applied to wet hair, and combed through to evenly distribute. Hair is then rolled onto curler as specified and dried in a 100° C. over for one (1) hour, then overnight at room temperature on a flat surface. |

D. Calculations

1. Calculate percent curl retention as follows:

$$\% \text{ Curl Retention} = \frac{(Lo) - (Lt)}{(Lo) - (Li)} \times 100$$

Where:
Lo=length of fully extended hair
Li=lengths of hair before exposure (initial)
Lt=length of hair after exposure 2. Use Lotus 123 program for data entry and graph generation.

E. References

The Aerosol Handbook, Montfort A. Johnson, "High Humidity Curl Retention Testing", p. 432.

3. DRYING TIME AND STICKINESS/TACKINESS OF HAIRSPRAYS (Trained Panel Method)

As solvent evaporates from freshly applied hairspray, the formulation experiences a period of time during which it is sticky to the touch. This effect is due to the plasticizing action of the solvent and is influenced by a number of factors. Among these are heaviness of the spray, temperature, air movement, intrinsic tendency of a formulation toward stickiness and its propensity for solvent retention. In this test, the first three factors are controlled while stickiness and total drying time of a formulation are determined.

EQUIPMENT:

3½ gram hair swatches (virgin brown European hair) cut to 6½ length.
Lab Timer or Stopwatch.
Pump or Aerosol prototype to test.

PROCEDURE: (3 to 5 replicates are normally run).

1. Suspend hair swatch vertically from tress board.
2. Apply a controlled amount of product to hair tress from an 8" distance. For pumps apply two (2) spray depressions to front of tress. For aerosols apply a two (2) second burst to front of tress.
3. Start timer and have participant evaluate tresses.
4. Feel the entire length of tress with hands and indicate when hair (a) starts being sticky/tacky, (b) stops being sticky/tacky and (c) is completely dry.
5. Total drying time and duration of the sticky period can therefore be determined for the test and control samples.

NOTE To minimize right-handed bias, alternate hands when evaluating samples.

REPORT:

An average of 3–5 evaluations per sample.

4. INITIAL CURL DROOP

Measure the amount of curl droop of hair after being sprayed to simulate the real world experience of a consumer when they spray their hair and the actual loss of "hold" of the hairstyle that takes place before it dries.

EQUIPMENT/MATERIALS:

1. Hair tress (length: 6.5 weight: 2 gram) rolled in a spiral.
2. Bobby pins.
3. Stopwatch or timer.
4. Rollers—⅝" outer diameter.
5. Tress board with ¼" delineated lines.

PREPARATION OF HAIR:

1. All the hair is thoroughly washed and while still wet, rolled in a spiral curl diagonally on a ⅝" roller, and secured with bobby pins at each end.

Note; the spirals should not overlap each other, but be covering the entire curler.

2. The tresses are dried overnight, or placed in a 45° C. oven for one (1) hour, or placed under a salon hair dryer for one (1) hour.

3. Before spraying the hair the rollers are carefully removed, trying to maintain the curl as tight as possible.

4. The tress is then sprayed with the product and the curl droop is measured every minute for ten (10) minutes.

5. Application is determined using the following chart;

| Hair Spray Type | Distance from Curl | Amount of Product Applied |
|---|---|---|
| Pump | 8" | 4 depressions - front only |
| Aerosol | 8" | 4 seconds - front only |

6. The conditions, ideally, should be 70° F. and 50% relative humidity. Six (6) swatches are tested for each variable and the data compared statistically using the following formula, and worksheet;

$$1 - \frac{lo - lf}{lo - li} \times 100$$

lo=original length, fully extended hair
li=initial length curled, before drying
lf=final length curl, after drying While the invention has been described with particular reference to certain embodiments thereof, it will be understood that changes and modifications may be made which are within the skill of the art. Accordingly, it is intended to be bound only by the following claims, in which:

What is claimed is:

1. A hair spray composition containing 80% or less VOC consisting essentially of, by weight,
   (a) about 0.5–12% of an ethyl or butyl half-ester copolymer of maleic anhydride and methyl vinyl ether, which is made by
      (i) copolymerizing the monomers in a solvent, by free radical polymerization, at a temperature of about 60° to about 90° C., in the presence of about 0.05 to about 10% by weight of maleic anhydride monomer of a polymerization initiator whose decomposition fragments are soluble in a 55% VOC hydroalcoholic composition, and
      (ii) esterifying the copolymer solution, wherein the copolymer is crystal clear and has a weight average molecular weight of about 30,000 to about 120,000, a polydispersity of less than about 2.5, and a specific viscosity of about 0.25 to about 0.39,
   optionally neutralized in an amount of up to about 25 mole %,
   (b) 0–80% ethanol,
   (c) 19–99% water, and
   (d) 0–35% propellant,
   said composition being crystal clear in appearance, has a Brookfield viscosity of less than about 30 cps at a 5% solids level, and forms clear films having a high humidity curl retention of at least about 90%, a tack time below about 30 seconds, and a dry time of below about 45 seconds, and which forms spray particles of less than about 100 μm in a pump system, and of less than about 80 μm in an aerosol system.

2. A hair spray composition according to claim 1 wherein said copolymer has a weight average molecular weight of about 50,000 to about 100,000, and a polydispersity of about 1.8 to about 2.2.

3. A hair spray composition according to claim 2 wherein said weight average molecular weight is about 60,000 to about 80,000.

4. A pump hair spray composition according to claim 1 which does not contain a propellant.

5. An aerosol hair spray composition according to claim 1 in which a propellant is present therein.

6. A hair spray composition according to claim 1 wherein said copolymer is the ethyl half-ester copolymer.

7. A hair spray composition according to claim 1 wherein said copolymer is included therein as a 50% ethanolic solution of the copolymer.

8. A hair spray composition according to claim 1 wherein said copolymer is neutralized in an amount of up to about 25 mole %.

9. A hair spray composition according to claim 1 wherein the polymerization initiator is present in an amount of about 1 to about 5% by weight of maleic anhydride monomer using an azo initiator having a 10-hour half-life of about 60° to about 70° C.

10. A hair spray composition according to claim 1 wherein the polymerization initiator is an azobis compound having a solubility in water of 0.5 g./100 g. of water.

11. A hair spray composition according to claim 10 wherein said azobis compound is selected from the group consisting of 1,1'-azobis (1-cyclohexanecarbonitrile);
2,2'-azobis (N,N'-dimethyleneisobutyramidine) dihydrochloride;
2,2'-azobis(2-amidinopropane) dihydrochloride;
2,2'azobis(N,N'-dimethyleneisobutyramidine);
4,4'-azobis(4-cyanopentanoic acid);
2,2'-azobis{2-methyl-N-[1,1-bis(hydroxymethyl)-2-hydroxyethyl]propionamide};
2,2'-azobis{2-methyl-N-[1,1-bis(hydroxymethyl)ethyl]propionamide};
2,2'-azobis[2-methyl-N-(2-hydroxyethyl) propionamide; and
2,2'-azobis(isobutyramide) dihydrate.

12. A hair spray composition according to claim 11 wherein said azobis compound is 4,4'-azobis(4-cyanopentanoic acid).

13. A hair spray composition according to claim 1 which is an aerosol system containing a can corrosion inhibitor.

14. A hair spray composition according to claim 1 which contains ethanol in an amount of up to 55%.

15. A hair spray composition according to claim 6 wherein the specific viscosity of the copolymer is about 0.28 to about 0.35 as a 1% solution of the copolymer in ethanol.

16. A hair spray composition according to claim 1 wherein said VOC level is 55% or less.

17. A hair spray composition according to claim 1 in which esterification of the copolymer is carried out in the absence of an esterification catalyst.

* * * * *